(12) United States Patent
Yao et al.

(10) Patent No.: US 9,758,754 B2
(45) Date of Patent: Sep. 12, 2017

(54) CELL SEPARATION AND CULTURE DEVICE

(71) Applicant: National Tsing Hua University, Hsinchu (TW)

(72) Inventors: Da-Jeng Yao, Hsinchu (TW); Chih-Chung Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 248 days.

(21) Appl. No.: 14/608,676

(22) Filed: Jan. 29, 2015

(65) Prior Publication Data

US 2016/0122699 A1   May 5, 2016

(30) Foreign Application Priority Data

Oct. 31, 2014 (TW) .............................. 103137844 A

(51) Int. Cl.
*C12M 1/00* (2006.01)
*C12N 1/22* (2006.01)
*C12M 1/12* (2006.01)

(52) U.S. Cl.
CPC ............ *C12M 23/20* (2013.01); *C12M 25/02* (2013.01); *C12M 47/02* (2013.01); *C12N 1/22* (2013.01)

(58) Field of Classification Search
CPC ...... C12M 23/20; C12M 25/02; C12M 47/02; C12M 21/02; C12N 1/12; C12P 7/6463; C12P 7/649; A01G 33/00
See application file for complete search history.

(56) References Cited

U.S. PATENT DOCUMENTS

2004/0086423 A1* 5/2004 Wohlstadter .......... G01N 21/66
                                                                 422/52
2011/0250626 A1* 10/2011 Williams ............... C12Q 1/527
                                                                 435/18

OTHER PUBLICATIONS

Chih-Chung Chen et al., "Paper-Based Device for Single Microalgae Separation and Cultivation", Institute of NanoEngineering and MicroSystems, National Tsing Hua University, Hsinchu City 300, Taiwan, ROC.

* cited by examiner

*Primary Examiner* — Michael Hobbs
(74) *Attorney, Agent, or Firm* — WPAT, P.C., Intellectual Property Attorneys; Anthony King

(57) ABSTRACT

A cell separation and culture device having a porous substrate; and a patterned carbon powder layer having a plurality of hollow regions, formed on an upper surface of the porous substrate by a forming manner; wherein the thickness of the patterned carbon powder layer is 0.04-0.08 mm. The cell separation and culture device is able to separate, detect or culture cells with various size and shape. The cell separation and culture device of present invention also simplifies the process of cell separation, detection and culture; therefore, it is accomplished within a very short time.

12 Claims, 5 Drawing Sheets
(3 of 5 Drawing Sheet(s) Filed in Color)

(A)

(B)

(C)

(D)

(E)

(A) (B)

(C) (D)

CELL SEPARATION AND CULTURE DEVICE

CROSS-REFERENCE TO RELATED APPLICATIONS

This application claims the priority benefit of Taiwan application serial no. 103137844, filed on 31 Oct. 2014. The disclosure of the Taiwan application is incorporated by reference herein.

BACKGROUND OF THE INVENTION

1. Field of the Invention

The present invention relates to a cell separation and culture device, especially relates to a cell separation and culture device comprising a porous substrate and a patterned carbon layer.

2. The Prior Arts

The cell separation techniques are frequently used by scientists who study in microbiology, zoology or botany, because the microbial cells, animal cells or plant cells are all existed in the mixture form in nature. If we want to obtain a specific cell or a specific cell species, we have to separate or isolate the cell(s) from numerous and various cells, and then use the cell to further analysis or various experiments.

In general, the operators in the art often use centrifugation with manually picking way to separate to target cells. The centrifugation step is used to subsiding heavier cells, and then depends on the characteristic of the target cells are suspending or precipitation, take the suspension or precipitate and pick out the target cell by using microscope. However, even we can roughly take the suspension or precipitate according to its characteristic, it still contains several kinds or even dozens of kinds of cells in the suspension or precipitate. Accordingly, the work under microscope requires much time and effort.

In addition, the separated cells can't be obtained their property via experiment or apply for other application in most circumstances due to the insufficient numbers of cells. Thus doing cell culture process after cell separation to increase the number of cells is needed. In doing cell culture process, we primarily transfer the separated cells to each well of culture plate using a micropipette. The work of operating a micropipette to transferring a certain number of cell, adding the cell medium or replacing the cell medium in each well of culture plate also requires much time and effort.

Therefore, a cell separation and cell culture device or method for saving time and effort would be useful for the cell separation and cell culture operators in the art.

SUMMARY OF THE INVENTION

To solve the problem, the present invention provides a cell separation and culture device, comprising: a porous substrate; and a patterned carbon layer having a plurality of hollow regions, formed on an upper surface of the porous substrate by a forming manner; wherein the thickness of the patterned carbon layer is 0.04-0.08 mm; and the forming manner is adsorption, transfer printing or coating manner.

In one embodiment of the present invention, the thickness of the porous substrate is 1-3 mm, and the average pore size of the porous substrate is 2-8 μm.

In another embodiment of the present invention, the porous substrate is a filter paper and it is made of cotton fibers, wooden fibers, carbon fibers, hemp fiber, quartz fibers or any combination thereof. Those fibers each or combination to be interlaced to form porous structure of filter paper, then could be applied to the porous substrate of the device.

In another embodiment of the present invention, the size of the plurality of hollow regions is 150 μm-1 mm. In some circumstance, the size of the plurality of hollow region could be 150-500 μm.

In further embodiment of the present invention, an absorbent material laid under the porous substrate; in a preferred embodiment, the device further comprising a waterproof material equipped on the patterned carbon layer to form at least one partition, wherein the waterproof material is silicone or a waterproof fixture.

Another aspect of the present invention is related to a cell separation method, comprising: providing a solution containing one or more cells to be separated; and allowing the solution to pass through the cell separation and culture device described above.

The cell separation method further comprising an absorbent material laid on a lower surface of the porous substrate to generate a fluid suction force for facilitating the solution's flow; in a preferred embodiment, further comprising a waterproof material equipped on the patterned carbon layer to form at least one partition, wherein the waterproof material is silicone or a waterproof fixture.

Another aspect of the present invention is related to a cell culture method, comprising: placing one or more cells to be cultured in at least one of the plurality of hollow regions of the device described above; and filling the pores of porous substrate with a medium.

The cell culture method further comprising an absorbent material laid on a lower surface of the porous substrate to generate a fluid suction force for facilitating the solution's flow; in a preferred embodiment, further comprising a waterproof material equipped on the patterned carbon layer to form at least one partition, wherein the waterproof material is silicone or a waterproof fixture.

In one embodiment of the present invention, the placing step comprises allowing a solution containing cell to be cultured to pass through the device described above.

By the features of the present invention, the efficiency of isolating single cell from a mixed microalgae population is over 700% superior to conventional serial dilution method. It could work as an incubator and be operated with a common lab micropipette by the open-structure design. The cell separation and culture device could separate, exam or culture cells (such as algae cells, animal cells and plant cells) with various shape and size. We also could simplify the process of cell separation by using the cell separation and culture device, thus significantly reduce the time cost. Thus, an easy-to-handle, simple fabrication, disposable and affordable device enabling single cell separation is demonstrated. Further, we could do observation, examination or culture cells after separation without moving the cells. Therefore, we could solve the time-consuming and work-consuming problems by using the cell separation and culture device.

The preferred embodiments described below are disclosed for illustrative purpose but to limit the modifications and variations of the present invention. Thus, any modifications and variations made without departing from the spirit and scope of the invention should still be covered by the scope of this invention as disclosed in the accompanying claims.

BRIEF DESCRIPTION OF THE DRAWINGS

The patent or application file contains at least one drawing executed in color. Copies of this patent or patent application

DETAILED DESCRIPTION OF THE PREFERRED EMBODIMENTS

Figure 1:
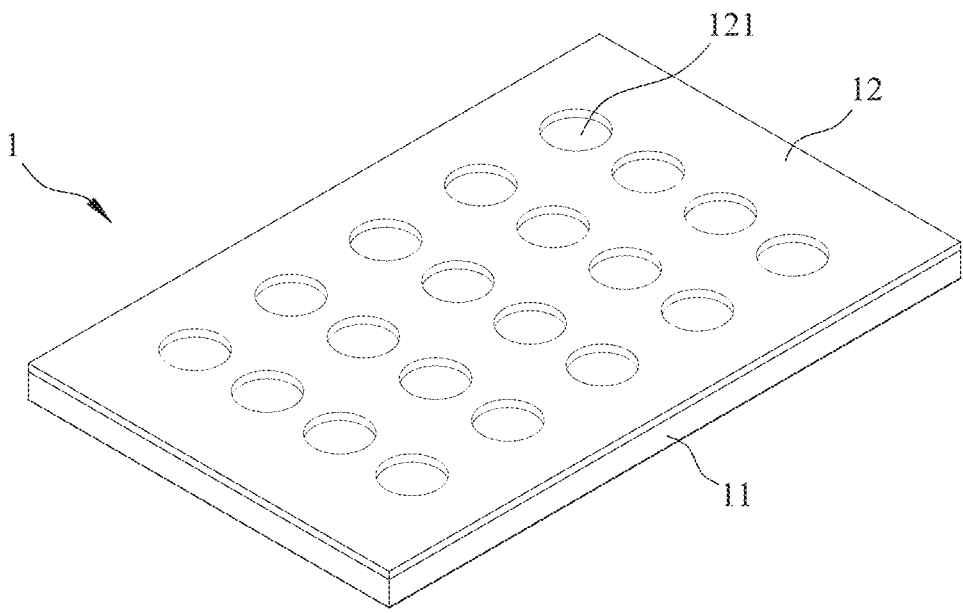
FIG. 1 is a schematic diagram showing the cell separation and culture device of the present invention.

FIG. 1 is a schematic diagram showing the cell separation and culture device of the present invention. Please refer to FIG. 1, the cell separation and culture device 1 of the present invention comprising: a porous substrate 11; and a patterned carbon layer 12 having a plurality of hollow regions 121, formed on an upper surface of the porous substrate 11 by a forming manner, thus we could see a part of the upper surface of porous substrate 11 through the hollow regions 121; wherein the thickness of the patterned carbon layer 12 is 0.04-0.08 mm.

The preferred thickness of porous substrate 11 is 1-3 mm. While the thickness is more than 3 mm, it increases unnecessary weight; on the other hand, while the thickness is less than 1 mm, the porous structure would tend to be shaky.

The porous substrate 11 could be any substrate having a plurality of pores that the average pore size within 2-8 μm, such as but not limit to porous paper and porous plastic plates. The cell separation speed would be reduced while the average pore size is too small. In contrast, while the average pore size is too large would allow the cells easily pass through the pores and thereby could not be separated. In addition, one skilled in the art could choose suitable pore size to implement the cell separation and culture device according the size of the cells to be separated, that is, the size of the cells to be separated must be greater than the average pore size.

The preferred porous substrate 11 is a filter paper, which is made of cotton fibers, wooden fibers, carbon fibers, hemp fiber, quartz fibers or any combination thereof. Those fibers each or combination to be interlaced to form porous structure of the filter paper, then could be applied to the porous substrate 11 of the device 1.

As previously mentioned, the patterned carbon layer 12 having a plurality of hollow regions 121 and formed on the upper surface of the porous substrate 11 by a forming manner; the preferred thickness of the patterned carbon layer 12 is 0.04-0.08 mm; the preferred forming manner is include but not limit to adsorption, transfer printing or coating. The patterned carbon layer 12 used to form a plurality of solution passing region (hollow regions 121), leading the flow rate of the solution containing cell to be separated is various at different region of the cell separation and culture device 1, thereby allow cells to be retained at specific position. Further, because of the patterned carbon layer 12 having a thickness, the cells retained in the hollow region 121 are hard to flow out, thus the cell separation and culture device 1 is conferred the use of cell separation and cell culture.

The preferred size or diameter of plurality of hollow region 121 of patterned carbon layer 12 is 150 μm-1 mm. In some circumstance, the size of plurality of hollow region 121 could be 150-500 μm. When using the cell separation and culture device 1 to separate the cells to be separated, a cell retained in a hollow region 121 would block other cells to enter the hollow region 121 while the pore size (length or width if hollow region 121 has a rectangle shape; diameter if hollow region 121 has a circular shape) is suitable, thereby increase the probability of a single cell be retained in a single hollow region 121. Thus, the size of hollow region 121 is selectively according to the size of the cell to be separated, in most cases, the size of hollow region 121 is about 10 to 20 times larger than the size of the cell to be separated.

The method to produce the cell separation and culture device 1 is design the pattern of the patterned carbon layer 12 first, then prints the pattern onto the upper surface of porous substrate 11 to complete the patterned carbon layer 12. Further, if the thickness of the patterned carbon layer 12 is not enough, repeat printing process until the required thickness is achieved.

Figure 2:
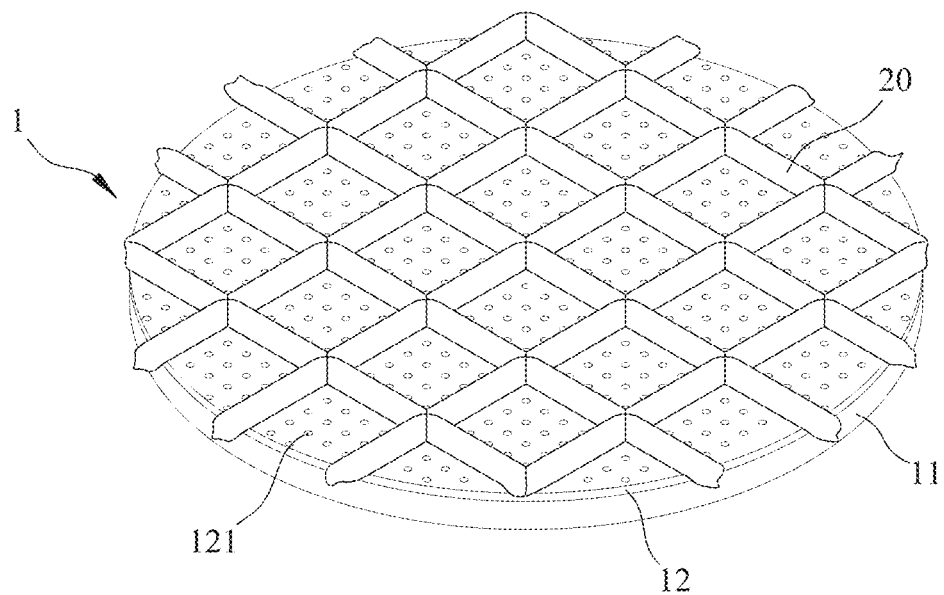
FIG. 2 is a schematic diagram showing a waterproof material equipped on the cell separation and culture device of the present invention to form partitions.

FIG. 2 is a schematic diagram showing a waterproof material 20 equipped on the cell separation and culture device 1 of the present invention to form partitions, the waterproof material include but not limit to silicone 20 or a waterproof fixture. Further, an absorbent material optionally laid under the cell separation and culture device 1 (on the lower surface of the porous substrate), the absorbent material include but not limit to paper towel, toilet paper, tissue paper, facial tissue and cambric. When using the cell separation and culture device 1, provide a solution containing more than one kind of cell to be separated and pull into the partitions, and wait for the entire solution pass through the cell separation and culture device 1, then finish the cell separation. If further observation or examination is needed after cell separation, we could remove the silicon 20 and put the device 1 under a microscope to observe or exam. It is no longer needed to move the cells on a slide for observation or examination.

In addition, if increase the number of the separated cell is needed, we could put the cell separation and culture device 1 into a container (such as a petri dish) containing a medium to keep the porous substrate 11 wet. It needs not spend much time and effort to move the cell to culture plate from each hollow region 121 using a micropipette. However, it is noted that the liquid level of the medium should not higher than the surface of the cell separation and culture device 1, avoiding the cells in the hollow region 121 flows out. Furthermore, we also could use silicon 20 or other fixture and jig to form partition to prevent the surface of the cell separation and culture device 1 be flooded by medium.

According to FIG. 2, one embodiment of the cell separation and culture device 1 could be divided into several areas by using silicon 20 or other fixture and jig. The pattern of patterned carbon layer 12 could be designed to different size or numbers of the hollow region 121 in different region to fit various cell or examination. Optionally, the pattern of patterned carbon layer 12 could be designed to different size of the hollow region 121 according to rows or columns in one area.

An exemplary example of the cell separation and culture device 1 applied for algae cell separation, observation and culture is described below. Algae lives in the water such as in pond, lake or river, the species of algae in water depends on its environment. Thus, we could get the environment information such as sunlight condition and bacteria species around the environment through obtaining the distribution of algae species in the environment. However, due to the algae has various shape and size, we usually put the water such as lake water or pond water under a microscope and sorting manually. By using the cell separation and culture device 1, we can separate, observe, or culture the cells in very fast and convenient way.

Example 1: Results of Cell Separation

A filter paper having a thickness of 2 mm and average pore size of 3 μm printed repeated 12×8 circular hollow region patterns by a carbon powder printer. The diameter of each hollow region is 500 μm. Repeat print the same pattern three times and complete the production of the cell separation and culture device 1.

To confirm the cell separation result by using the cell separation and culture device 1, the cells to be separated include cells with various shape and size. First, we prepare an aqueous solution containing *Cosmarium* sp., *Haemalococcus ptuvialis* and *Arthrospira* sp. to simulate the condition of mixing population in nature, and test the separation result using the cell separation and culture device 1.

Figure 3:
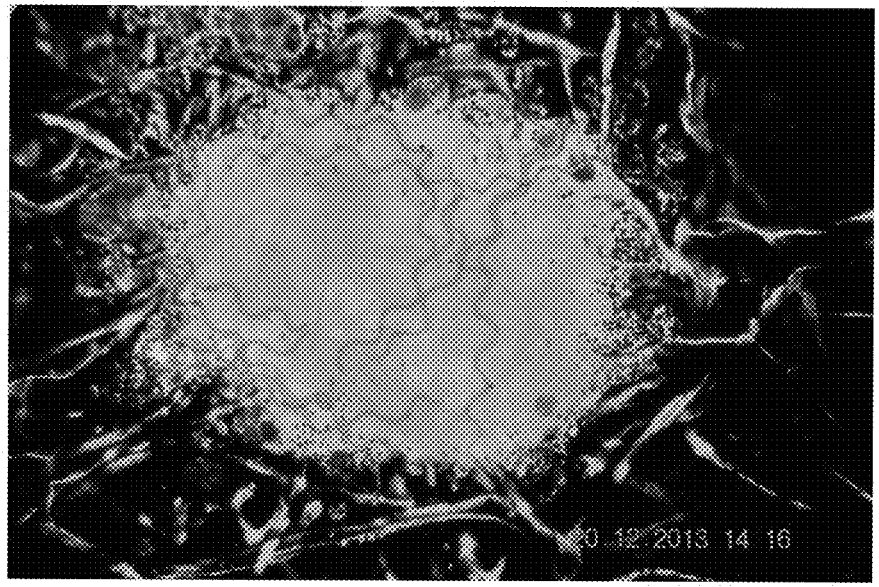
FIG. 3 show that the hollow regions of the cell separation and culture device of the present invention after separating algae cell contained solution with various concentrations. (A) the concentration of algae cell contained solution is 200 cell/ml; (B) the concentration of algae cell contained solution is 50 cell/ml; (C-E) the concentration of algae cell contained solution is 33 cell/ml, and show single *Cosmarium* sp. cell, single *Haemalococcus ptuvialis* cell and single *Arthrospira* sp. cell in a single hollow region, respectively.
Figure 3:
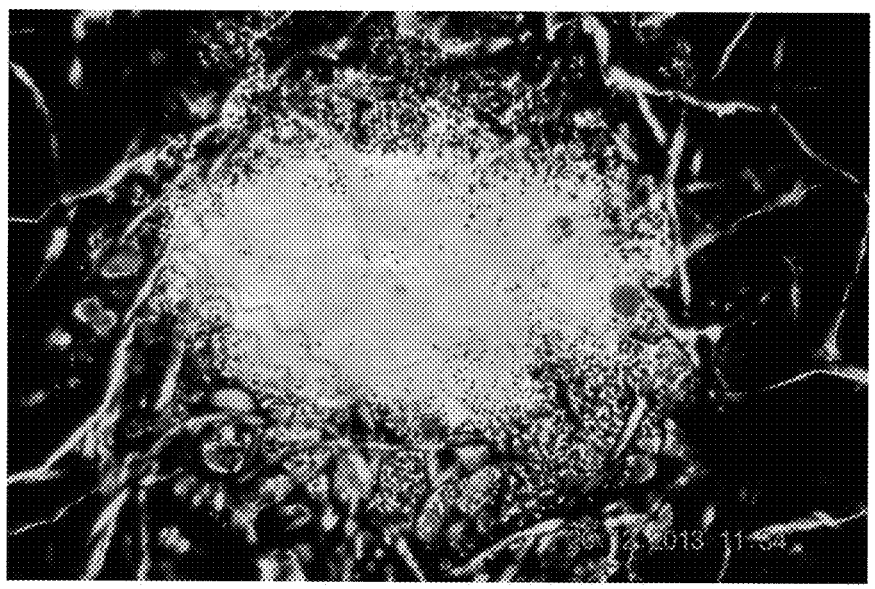
Figure 3:
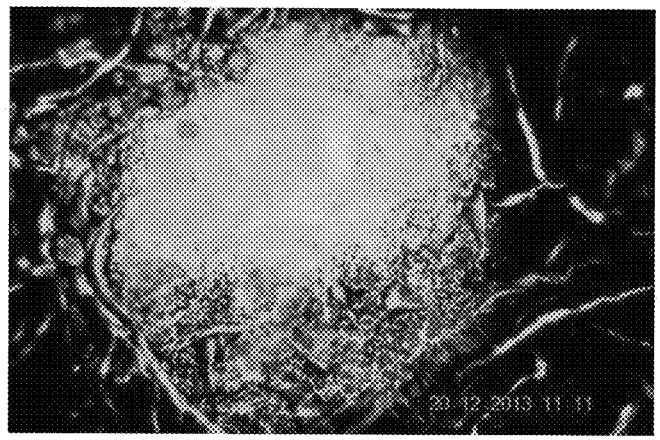
Figure 3:
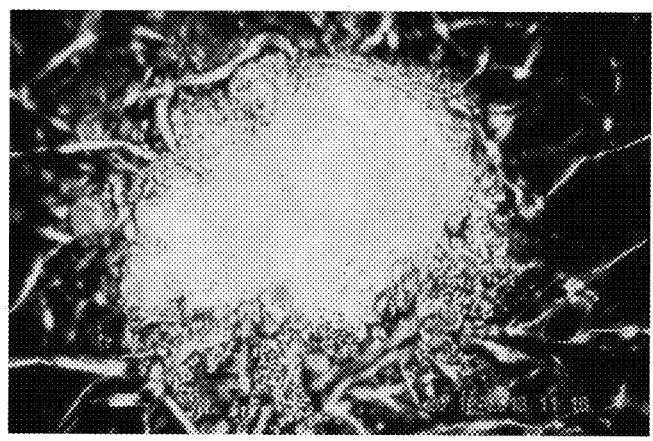
Figure 3:
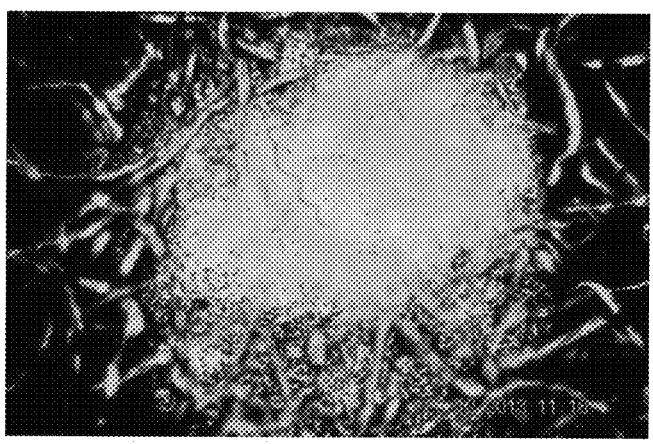
Figure 4:
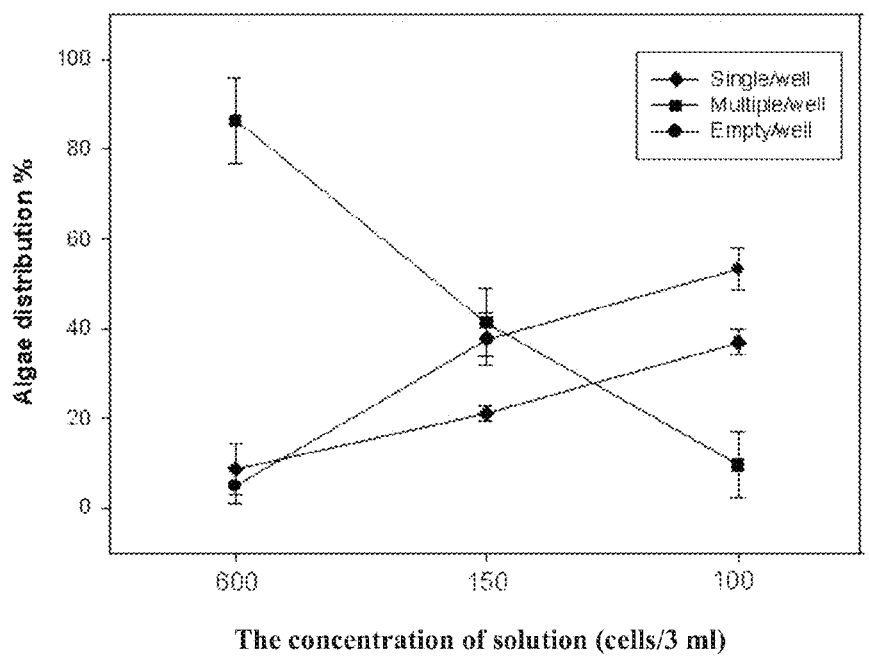
FIG. 4 is a diagram showing the separation efficiency of algae cell contained solution with various concentrations by using the cell separation and culture device of the present invention.

We use silicone 20 to form partitions on the cell separation and culture device 1, and laid a stack of paper towel under the cell separation and culture device 1, then pour 3 ml solution prepared above into each partition. The paper towel absorb the solution and generate a fluid suction force, in consequence, the flow rate at the hollow regions would be greater than at carbon powder covered regions, thereby the algae cells in the solution would be retained in the hollow regions. We remove silicon 20 and put the cell separation and culture device 1 under a microscope, the microscopic observation results are showed in FIG. 3. FIG. 3A shows the separation result of high concentration algae solution (200 cells/ml), there are multiple algae cells in each hollow region 121. FIG. 3B shows the separation result of medium concentration algae solution (50 cells/ml), there are still several algae cells in each hollow region 121. FIG. 3C-E shows the separation result of low concentration algae solution (33 cells/ml), one single algae cell in many hollow region 121 could be found. Among the concentrations of 200 cells/ml, 50 cells/ml and 33 cells/ml, the concentration of 33 cells/ml has best separation efficiency as showed in table 1 and FIG. 3. Table 1 shows the cell separation result of algae cell solution with various concentrations, the lower concentration of algae cell solution showed the better single cell separation efficiency. FIG. 4 shows the separation result as a diagram. The separation efficiency can reach 37% in average for isolating single cell per well which is over 700% superior to current serial dilution method which is usually capable of around 5% efficiency for single cell isolation.

TABLE 1 the cell separation result of solution containing algae cells in different concentrations

| | Concentrations of solution containing algae cells Cell number/hollow region | | |
|---|---|---|---|
| | 100 cells/3 mL | 150 cells/3 mL | 600 cells/3 mL |
| Single algae cells | 37% | 21% | 9% |
| No algae cells | 53% | 38% | 5% |
| Multiple algae cells | 10% | 41% | 86% |

Figure 5:
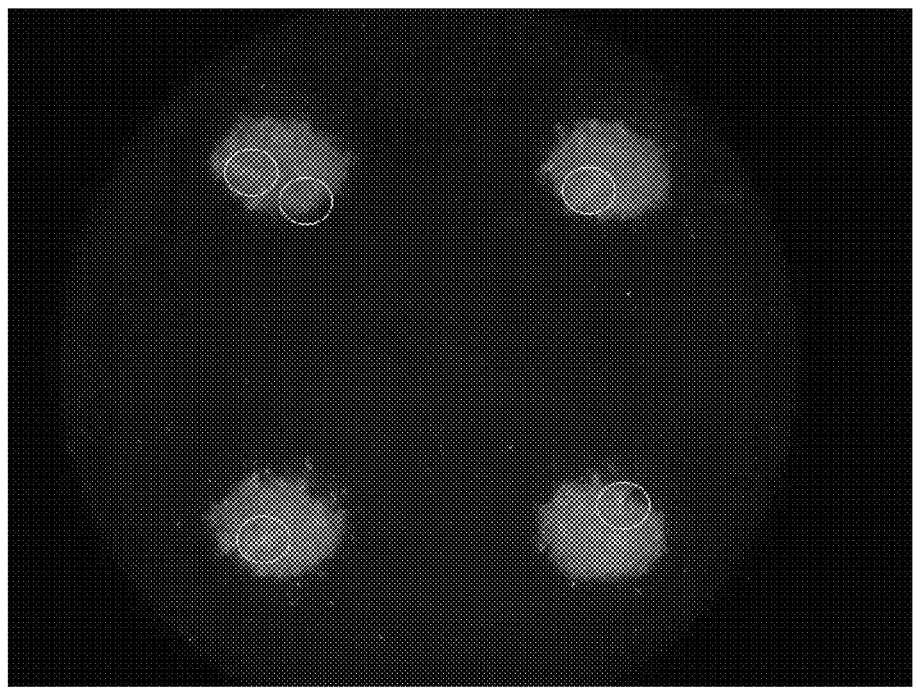
FIG. 5 is a fluorescent image showing the position of the separated fluorescent *Arthrospira* sp. cell, confirmed that the separated cell only retain in the hollow regions.

In order to demonstrate the algae cells are only retained in hollow region 121, the result obtained by a fluorescent microscope showed in FIG. 5. FIG. 5 shows all fluorescent *Arthrospira* sp. after separation (the circles in the Figure) exists in hollow region 121, confirmed that the separated cells are only retained in hollow region 121.

Example 2 Results of Separated Cells Culture

The cell separation and culture device 1 with separated cells of Example 1 works as an incubator by rinsing the porous substrate with growth medium. We put the cell separation and culture device 1 into a petri dish containing an algae medium to keep the device 1 wet. It is noted that the liquid level of the medium should not higher than the surface of the cell separation and culture device 1, avoiding the algae cells flows out. Furthermore, we also could use silicon 20 or other fixture and jig to form partition to prevent the surface of the cell separation and culture device 1 be flooded by medium.

Figure 6:
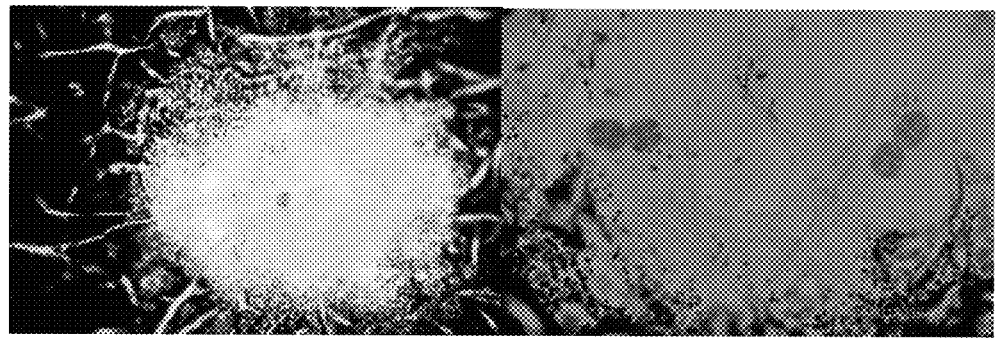
FIG. 6 show that the single desmid cell grows in the hollow regions with cultured for (A) 0 day, (B) 3 weeks, (C) 8 weeks, and (D) 10 weeks after the cells be separated.
Figure 6:
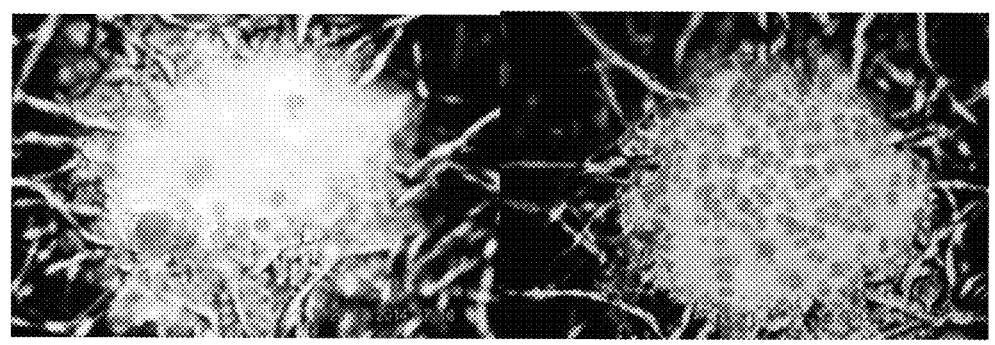

The results of the single *Cosmarium* sp. cell grows in the device 1 with cultured 0 day, 3 weeks, 8 weeks, and 10 weeks are showed in FIG. 6 A-D, indicates that the number of *Cosmarium* sp. cell significantly increases with time. It reveals the microalgae could be cultured from one single isolated cell to a population in the device 1 after 8 weeks cultivation. The result confirmed that the device 1 is a good cell culture device.

According to the examples described above, we could simplify the process of cell separation by using the cell separation and culture device 1, thus significantly reduce the time cost. Further, we could do observation, examination or culture cells after separation without moving the cells. Therefore, we could solve the time-consuming and work-consuming problems by using the cell separation and culture device 1.

What is claimed is:

1. A cell separation and culture device, comprising:
   a porous substrate having a plurality of pores, the average pore size of the porous substrate is 2-8 μm; and
   a patterned carbon layer having a plurality of hollow regions, formed on an upper surface of the porous substrate by a forming manner; the size of the plurality of hollow regions is 150 μm-1 mm and the position of the plurality of pores and the plurality of hollow regions is not related;
   wherein the thickness of the patterned carbon layer is 0.04-0.08 mm; and the forming manner is adsorption, transfer printing or coating manner.

2. The device of claim 1, wherein the porous substrate is a filter paper.

3. The device of claim 2, wherein the filter paper is made of cotton fibers, wooden fibers, carbon fibers, hemp fiber, quartz fibers or any combination thereof.

4. The device of claim 1, wherein the thickness of the porous substrate is 1-3 mm.

5. The device of claim 1, wherein the size of the plurality of hollow regions is 150-500 μm.

6. The device of claim 1, further comprising an absorbent material laid on a lower surface of the porous substrate.

7. The device of any one of claim 1, further comprising a waterproof material equipped on the patterned carbon layer to form at least one partition; wherein the waterproof material is silicone or a waterproof fixture.

8. A cell separation and culture method, comprising:
   providing a solution containing one or more cells to be separated and cultured;
   allowing the solution to pass through the cell separation and culture device of claim 1, thereby the cells are retained in the hollow region; and
   filling the pores of porous substrate with a medium.

9. The method of claim 8, wherein the porous substrate is a filter paper.

10. The method of claim 8, further comprising an absorbent material laid on a lower surface of the porous substrate to generate a fluid suction force for facilitating the solution's flow.

11. The method of claim 8, further comprising a waterproof material equipped on the patterned carbon layer to form at least one partition; wherein the waterproof material is silicone or a waterproof fixture.

12. The method of claim 8, wherein the cell to be separated and cultured is algae cell, animal cell or plant cell.

\* \* \* \* \*